United States Patent [19]

Shackleford et al.

[11] 4,361,148

[45] Nov. 30, 1982

[54] FLEXIBLE CONDUIT WITH RELEASABLE SEALING MEANS

[75] Inventors: John E. Shackleford, Walnut Creek; Willie J. Lewis, Oakland, both of Calif.

[73] Assignee: Cutter Laboratories, Inc., Berkeley, Calif.

[21] Appl. No.: 212,481

[22] Filed: Dec. 3, 1980

[51] Int. Cl.³ ............................................. A61M 5/00
[52] U.S. Cl. ................................. 128/214 D; 128/274
[58] Field of Search .............................. 251/358, 4, 9; 128/214 D, 272, 272.3, 272.1, 274, 247

[56] References Cited

U.S. PATENT DOCUMENTS 2,922,613  1/1960  Beachman et al. ............... 251/4
3,064,647  11/1962  Earl ................................ 128/214 D

FOREIGN PATENT DOCUMENTS 1280708  11/1961  France .......................... 128/214 R Primary Examiner—Richard J. Apley
Assistant Examiner—T. J. Wallen
Attorney, Agent, or Firm—Robert E. Allen

[57] ABSTRACT

A means for releasable sealing a flexible conduit is disclosed, having particular use in a conduit connecting multiple blood bags. The conduit contains within a portion of itself a flexible strip or tubular insert. This portion of the conduit is positively closed by folding it back on itself and the closed portion is maintained by a clamping or restraining member. Upon release of the clamping member following a heat sterilization procedure, the conduit is readily opened for fluid flow therethrough. The conduit, which without the insert would normally be fused together as a consequence of the heat sterilization, is open by virtue of the insert being made of a material which does not fuse together under these conditions.

7 Claims, 8 Drawing Figures

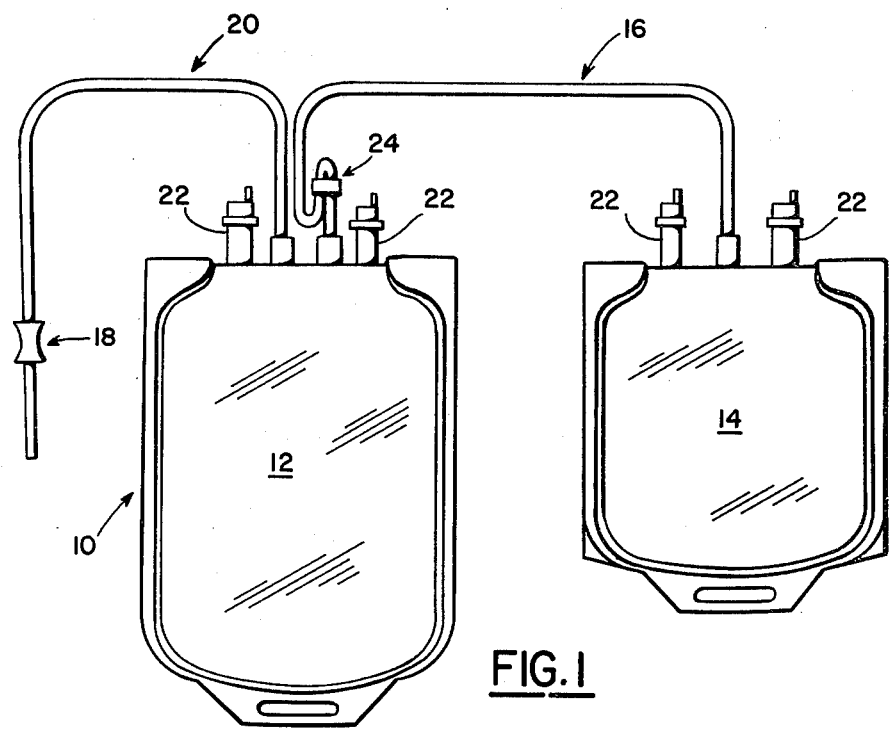
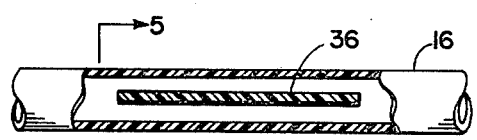
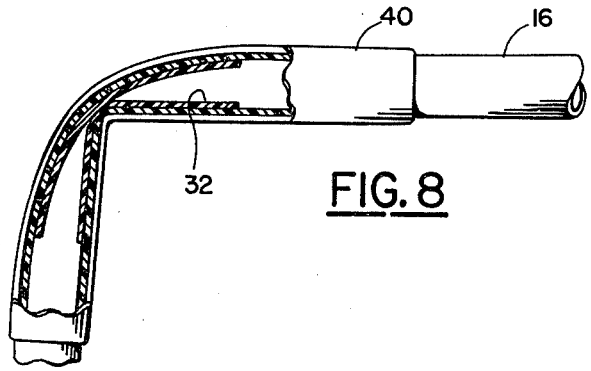

4,361,148

FLEXIBLE CONDUIT WITH RELEASABLE SEALING MEANS

BACKGROUND OF THE INVENTION

1. Field of the Invention

This invention relates to means for blocking fluid flow in a flexible conduit, particularly in a conduit connecting two or more flexible containers as in a multiple blood bag system.

2. Prior Art

A variety of means have been developed for blocking the flow of fluid from one blood bag to another through interconnecting tubing until such time it is desired to transfer the fluid from one bag to another. Generally this has involved a valve system wherein a membrane closing fluid flow, which is located in the interconnecting tubing, is pierced by a cannula as shown in U.S. Pat. Nos. 3,110,308, and 3,685,795, or by a spike member such as in U.S. Pat. No. 4,195,632, to allow fluid to be transferred. It is also possible to block the flow of a fluid by the use of an external slide clamp such as those disclosed in U.S. Pat. Nos. 3,064,647 and 3,078,847.

However, there are several disadvantages in the use of such blocking means. Blood bag systems have an anticoagulant in the primary or donor bag for the purpose of preventing coagulation of blood collected therein. To render the system sterile, blood bags must be subjected to a sterilization cycle involving exposure to steam at about 115° C. for about 50 minutes. It has been found that the inner surfaces of conventional vinyl tubing become fused together at the point where the tubing is clamped as a result of heat sterilization. Fluid flow between the donor bag and a second or satellite bag is therefore blocked even after removal of the clamp. Even if the walls of the tubing do not fuse together, the slide clamp sometimes is ineffective in completely closing the tubing and leakage occurs. During heat sterilization, the tubing softens and can sometimes be cut by sharp edges of the clamp.

Other means for blocking flow through flexible tubing are disclosed in U.S. Pat. Nos. 2,895,475, 2,995,334, and 3,103,335. In each instance, the tubing is closed off by bending the tubing back on itself and applying a restraining device of some sort to maintain the tubing in this position. The tubing is thus pinched off at the folding point. In U.S. Pat. No. 2,922,613, a malleable metal pipe placed around the tubing can be bent to approximately 90° at which point the tubing becomes pinched off. Although these means are simple and easy to use to block fluid flow in flexible tubing, the problem of fusion of tubing walls as a consequence of heat sterilization would not be avoided by the use of such devices.

SUMMARY OF THE INVENTION

The present invention provides means for releasably blocking a flexible conduit to fluid flow through the conduit, a portion of the walls of the conduit being in a first condition of compression to close the lumen of the conduit while the conduit is exposed to heat sterilization, and thereafter the conduit being capable of a second condition whereby the lumen is open for fluid flow therethrough. In particular, the releasable blocking means for the conduit is especially useful in conjunction with a multiple blood bag system in which a first bag communicates with a second bag by way of the conduit.

More particularly, the releasable blocking means comprises a flexible insert positioned within a section of the conduit, the flexible insert being made of a material whose walls, when in compressible contact during a heat sterilization period, will not stick or fuse together after they are in an uncompressed state. The insert may take the form of a hollow tubular member, or a trough-like section, or even a strip for example. The size of the insert preferably is such that it fits snugly within the conduit. The section of the conduit which contains the insert is folded at an intermediate point at least until the orifice of the conduit is closed. A preferred position is one in which the conduit section is folded back on itself. The conduit section is maintained in its closed condition by an appropriate retaining or clamping means of sufficient strength to assure there will be no leakage of fluid through the folded section during normal operating procedures. The clamping means should also be of a type which can be more or less readily removable. A preferred clamping means is a band of resilient material such as rubber or the like which does not stick to the flexible conduit following heat sterilization. Bands of plastic or malleable metal can also be used. To initiate fluid flow through the conduit, the clamping means is merely slipped or pried off the folded section and the folded section can be quickly made to assume an unfolded open condition. Flow rates in the present conduit system are superior to those systems mentioned above which utilize a membrane piercing member since there is essentially nothing in the conduit to obstruct fluid flow after the conduit has been opened.

A further understanding of the invention can be obtained from the drawings and detailed description which follows.

DESCRIPTION OF THE DRAWINGS

FIG. 1 shows a multiple blood bag system employing the releasable blocking means of the present invention;

FIG. 4 is a view partly in cross section of a portion of a conduit containing a flexible insert in the form of a strip;

FIG. 5 is a view taken along the line 5—5 of FIG. 4;

FIG. 6 is a view in perspective of another form of flexible insert;

FIG. 7 is a cross-sectional view showing the insert of FIG. 6 positioned within a conduit; and FIG. 8 is a view partly in cross section of a flexible tubular insert in a conduit wherein the conduit is maintained in a closed position by a malleable clamping member.

DETAILED DESCRIPTION OF PREFERRED EMBODIMENTS

Figure 2:
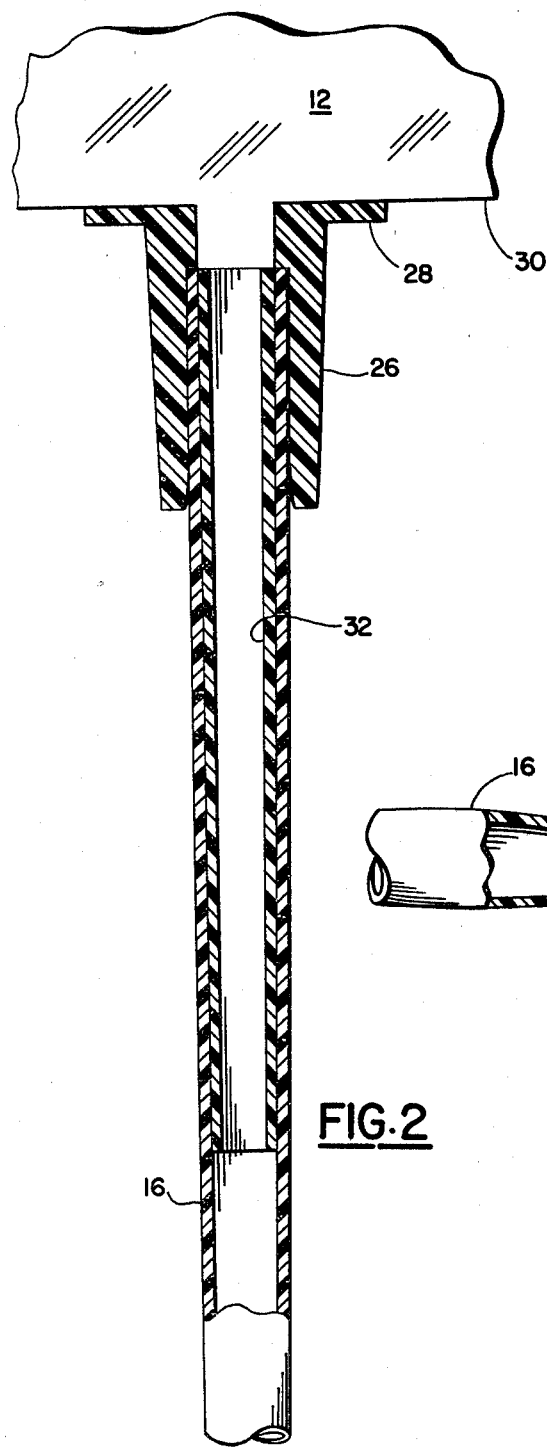
FIG. 2 is a view partly in cross section of a portion of a conduit which contains a flexible tubular insert, this portion of the conduit being joined to a transfer port on a flexible bag.

An example of a multiple blood bag system 10 is shown in FIG. 1 and comprises typically a donor or primary bag 12 connected by a flexible conduit 16 to a satellite or secondary bag 14. Each bag may have one or more sealed entry ports 22 and the donor bag 12 also has a flexible donor tube 20 attached at its outer end to a sealed phlebotomy needle 18. Bag 12 contains an appropriate anticoagulant solution. A releasably sealing means 24 which is the subject of this invention is generally located in a portion of the conduit 16 which is adjacent the donor bag 12.

Figure 3:
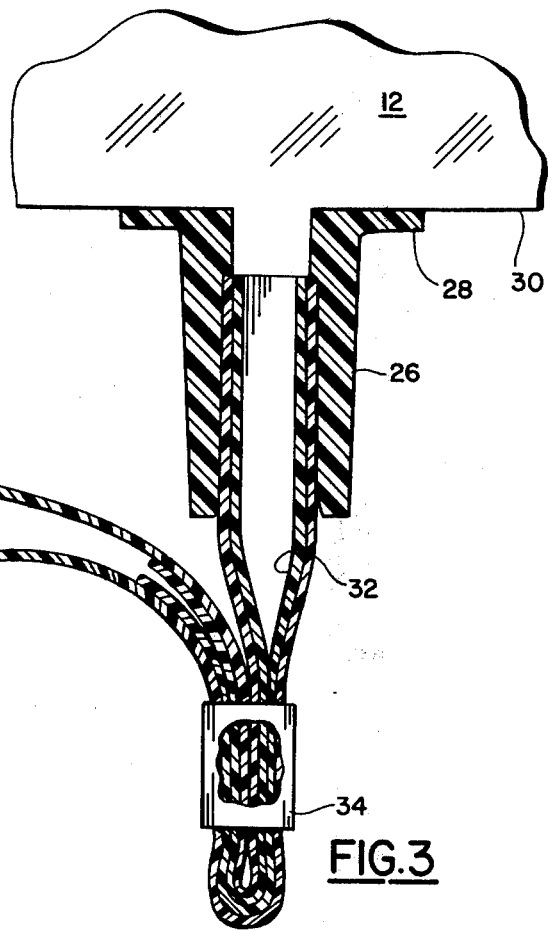
FIG. 3 is a view in partial cross section of the same conduit of FIG. 2 but showing the conduit bent back on itself and compressed in a closed position by a band.

A preferred embodiment of the releasable sealing means 24 can best be seen in FIGS. 2 and 3. Conduit 16 is sealed to and communicates with bag 12 via port 26. Port 26 may be bonded by its flange 28 to a wall 30 of bag 12 and conduit 16 may be sealed to the inner wall of port 26 by conventional means such as solvent bonding. Tightly encased within conduit 16 is a length of a flexible, resilient tubing insert 32, typically about 1.5 to about 2 inches long. Insert 32 is made of a material which does not stick or fuse together when the insert is compressed and subjected to the conditions of steam sterilization. Preferred materials are silicone or natural rubbers.

When the section of conduit 16 which contains the insert 32 is folded back on itself and a clamping member such as band 34 is placed around the folded portion as seen in FIG. 3, conduit 16 is effectively closed. Band 34 in this embodiment is a small tubular section of natural rubber. Other materials can also be used for band 34, e.g., non heat-fusing plastic; or the band can take the form of a malleable metal strip which encompasses the folded portion and which can subsequently be readily removed. The clamping member can take any form as long as it doesn't cut conduit 16 and effectively keeps conduit 16 closed until such time it is desired that it be opened.

Alternatives to the tubular insert 32 may take the forms shown in FIGS. 4–7. A strip 36 may be inserted within conduit 16 and is sufficiently wide so that its edges contact the inner walls of conduit 16 as shown in FIG. 5 with a degree of frictional engagement that prevents the strip from sliding within the conduit. Conduit 16 is folded over so that the flat surface of the insert 36 makes contact with itself. In like fashion, a curved strip insert 38 can be placed within conduit 16 as shown in FIG. 7 to function in a manner similar to inserts 32 or 36.

Conduit 16 containing insert 32 need not be folded back on itself to effect closure. For example, as shown in FIG. 8, by placing a malleable metal tube 40 around conduit 16 and bending tube 40 to an angle of about 90°, conduit 16 can be effectively closed. Tube 40 must be sufficiently malleable that it can be bent back into essentially a straight configuration and molded by the fingers at the previously bent portion to relieve kinking which may occur so that fluid flow may take place through conduit 16.

In practice, the multiple blood bag system with conduit 16 closed by the clamping member is subjected to steam sterilization. At the time of use, an appropriate quantity of blood may be drawn from a donor into bag 12. Following centrifugation of the bags and the blood in bag 12 which separates the red cells from the plasma, the clamping member is manipulated so as to open the lumen in conduit 16 whereby the plasma may be expressed into bag 14. In the situation where the clamping member is a rubber or plastic band, this can be readily removed either by cutting the band with bluntnosed scissors or by prying it off with a blunt ended instrument.

The means by which the conduit is releasably closed according to the teachings of this invention has proven highly satisfactory. During the rigors of heat sterilization and and centrifugation procedures that the system has been subjected to, there has been no leaking of anticoagulant or blood through the closed portion of conduit 16 in a large number of multiple blood bag sets tested.

While the invention has been described with particular reference to specific embodiments, other forms are possible without departing from the scope and spirit of the invention as defined by the appended claims.

We claim:

1. A multiple blood bag system comprising a first bag connected to a second bag by a flexible conduit having an internal diameter for fluid flow communication between the first and second bags and means for releasably sealing the conduit which comprises a flexible insert positioned within a section of the conduit, said flexible insert extending across said internal diameter and comprising a material which does not block said internal diameter when subjected to sterilization temperatures, the section of the conduit being bent back on itself, at least to a position wherein closure is established, and maintained in this position by a releasable clamping means to prevent fluid flow through the conduit.

2. The multiple blood bag system of claim 1 wherein the insert comprises a length of tubing of elastomeric material extending longitudinally within the section of the conduit.

3. The multiple blood bag system of claim 1 wherein the insert comprises a strip of elastomeric material extending longitudinally within the section of the conduit, the strip being at least as wide as the internal diameter of the conduit.

4. The multiple blood bag system of claims 2 or 3 wherein the insert is made of a material selected from the group consisting of natural rubber or a synthetic rubber.

5. The multiple blood bag system of claim 4 wherein the insert is made of silicone rubber.

6. The multiple blood bag system of claim 5 wherein the releasable clamping means comprises a band encircling and compressing the section of conduit containing the insert bent back on itself.

7. The multiple blood bag system of claim 6 wherein the band is made of rubber.

* * * * *